United States Patent [19]

Muller

[11] Patent Number: 5,057,268

[45] Date of Patent: Oct. 15, 1991

[54] METHOD AND COMPOSITION OF MATTER FOR DETECTING LARGE QUANTITIES OF PAPER CURRENCY

[75] Inventor: Richard A. Muller, Berkeley, Calif.

[73] Assignee: The MITRE Corporation, Bedford, Mass.

[21] Appl. No.: 629,994

[22] Filed: Dec. 19, 1990

[51] Int. Cl.[5] .................... G01N 23/221; G21G 1/12
[52] U.S. Cl. .................... 376/157; 250/271; 250/391; 250/392; 250/370.01; 385/85; 385/70
[58] Field of Search ............. 250/371, 271, 391, 392, 250/390.01, 370.04; 376/157, 159; 283/85, 70

[56] References Cited

U.S. PATENT DOCUMENTS 4,251,726  2/1981  Alvarez ........................... 396/157
4,980,569 12/1990  Crane et al. ...................... 283/85

Primary Examiner—Carolyn E. Fields
Assistant Examiner—Drew A. Dunn
Attorney, Agent, or Firm—Wolf, Greenfield & Sacks

[57] ABSTRACT

Paper notes used as a monetary currency are deuterated. The level of deuteration while not complete, is high. For U.S. currency the level of deuteration is at least 0.1 mg of deuterium for each one dollar in value of the currency note, and preferably at least 0.3 mg. Use of X-ray or gamma ray interrogation with a beam energy above 2 MeV produces a nuclear reaction releasing a neutron from the deuterium nucleus. If the currency is in large concentrations, e.g. $100,000 or more, the neutrons emitted by this reaction are reliably detectable. The deuteration occurs in the cellulose fibers forming the currency. To resist an exchange of hydrogen atoms for deterium atoms, the deuterium atoms can be used in the formation of synthetic cellulose where the deuterium is more deeply buried within the cellulose molecule than in naturally occurring cellulose. The deuterated synthetic fibers are blended with natural, non-deuterated fibers to form the paper. The currency can also include a mechanism, such as dye, to signal attempts to use solvents or otherwise facilitate any such hydrogen substitution.

10 Claims, 1 Drawing Sheet

METHOD AND COMPOSITION OF MATTER FOR DETECTING LARGE QUANTITIES OF PAPER CURRENCY

BACKGROUND OF THE INVENTION

This invention relates to non destructive interrogation techniques. More particularly, it relates to a deuterated paper currency and an x-ray interrogation of the currency to detect large concentrations of cash.

Illegal drug transactions are primarily for cash. Banking laws make it difficult, at least in the United States, to use the cash to hide its illegal origins. As a result, the illegal drug trade relies on the cash receipts from the sale of drugs to be smuggled out of countries with strict banking laws. Since drug sales usually involve currency notes of small denomination, the transfer of large amounts of money, e.g. more than $100,000, and certainly any shipments of $1,000,000 or more, the bulk of the cash to be smuggled becomes sizeable. For example, $1,000,000 in $20 notes, the most common denomination of U.S. paper currency used in illegal drug trafficking, is 50,000 notes each weighing about 1.1 g. The total weight of the $1,000,000 is then about 55 kg (121 pounds).

While the broad concept of tagging currency so that large concentrations of it can be detected is straightforward, its implementation is not so straightforward since any tagging must meet a variety of other criteria. It must be totally safe. There should be no radiation. The currency should not be a health hazard even if ingested. The tagging method must work at a comparatively long range so that standard overseas shipping containers (usually having an eight foot width) can be interrogated as well as smaller items such as luggage. The system should not be readily evaded by shielding. If shielded, the shielding itself should be readily detectable. The technique should not alter or injure the currency. The tagging should also not be detectable in low concentrations of money so that legitimate interests in privacy are not invaded. The tag should also be secure against removal. The tag and its associated detection equipment should also be cost effective.

Some possible non destructive tagging systems are enumerated in the discussion of the prior art in U.S. Pat. No. 4,251,726 to Alvarez. They include conventional x-ray scanning, barium tagging, nuclear magnetic resonance, vapor tagants, and chemical tagging. In general, however, simple shielding can foil these approaches, whether by blocking interrogating electromagnetic radiation or by trapping gases at the tagged article. None are suitable for use with currency. Conventional x-ray scanning equipment as used at airports will not reliably detect hidden bulks of ordinary paper currency.

The Alvarez patent itself discloses a method for tagging explosives. Alvarez teaches partially replacing hydrogen in the explosive with deuterium or beryllium. A linear accelerator produces a beam of 2 to 4 MeV x-rays arranged to interrogate luggage moving past the beam on a conveyor. These elements undergo a nuclear reaction, absorbing an x-ray photon and emitting a neutron. A boron triflouride neutron detector is able to distinguish the presence of neutrons from a deuterated explosive, if there are about $10^{23}$ deuterium atoms, or 0.3 gram, present in the explosive. Alvarez teaches that this level of deuteration is equivalent to a level twenty times that of enriched heavy water.

While this arrangement avoids the shielding drawback of barium tagging, it also alters slightly the chemical properties of the explosives. To the best of applicant's knowledge, the Alvarez system has not been in fact used because of these concerns with these changes in chemistry. Moreover, heretofore, there has not even been a suggestion that deuteration can or should be applied to control or monitor the movement of currency. One reason is the obvious hazards of x-rays and the creation of nuclear reactions in an item in wide public circulation. Another problem is that even if currency were fully deuterated, a prohibitive process for economic reasons alone, it is rare that there will be an accumulation of currency sufficient to be detectable. In sum, to date there is no known way to detect large amounts of cash concealed in shipping containers other than through a search of the container, which may destroy the container, and in any event would be impractical for routine screening of all containers moving out of country through standard commercial shipping channels.

It is therefore a principal object of the present invention to provide a new paper currency and an associated method for detecting paper currency reliably in large concentrations, while leaving the currency substantially undetectable in low concentrations.

Another principal object is to provide such a paper currency and associated method that is reliably effective at ranges that allow the interrogation of all standard shipping containers.

Still another principal object is to provide the foregoing advantages while introducing no safety hazard, such as radioactivity and toxicity if ingested.

A further object is to provide the foregoing advantages while also being substantially impervious to shielding, and if shielded, requiring shielding that is itself readily detectable.

Another object of the present invention is to provide a tagging method that does not alter or detract in any significant way from the desirable attributes of known paper currencies.

Yet another object is to provide the foregoing advantages at an acceptable cost using known equipment.

SUMMARY OF THE INVENTION

Notes of paper currency are highly deuterated at a level several orders of magnitude (preferably about 1,000 times) greater than used in any previously disclosed tagging arrangement. The level of deuteration for U.S. currency is at least 0.1 mg of deuterium for each one dollar value of the note, and preferably 0.3 mg. The deuterium is substituted for hydrogen atoms in the cellulose fibers forming the paper—cotton, linen, synthetic cellulose or a blend of two or more of these fibers. While the deuterium carbon bond is strong enough to resist a hydrogen-deuterium exchange if the currency is soaked in water, the deuterium may be bonded in a synthetic cellulose which is more resistant to such an exchange because the deuterium atom is buried more deeply within the molecule than is the case with naturally occurring cellulose. Synthetic fibers can, for example, constitute 10 to 20 percent by weight of the total fibers forming the paper. The fibers can also hold a mechanism, such as a dye, that is activated by an attempt to exchange hydrogen for deuterium, such as a solvent that promotes such an exchange.

The full detection system involves: 1) a source of x-rays having sufficient energy to produce a nuclear reaction causing the deuterium atoms to emit neutrons and 2) a detector of the emitted neutrons. The detector should slow the neutrons, to a "thermal energy" range, and must reliably detect the slowed neutrons. Conventional boron triflouride counters are preferred. To detect lead shielding of sufficient thickness to interfere with the x-ray interrogation, a secondary transmission x-ray device can be deployed to detect the shielding. If the shielding is directed to absorbing the emitted neutrons, there must be a mass of hydrogen rich material such as paraffin to thermalize the neutrons and a mass of boron to do the absorbing. If the shielding is not revealed by its own bulk, known detection systems for boron are available.

These and other features and objects of the invention will be more fully understood from the following detailed description, which should be read in light of the accompanying drawing.

DETAILED DESCRIPTION OF THE PREFERRED EMBODIMENTS

Figure 1:
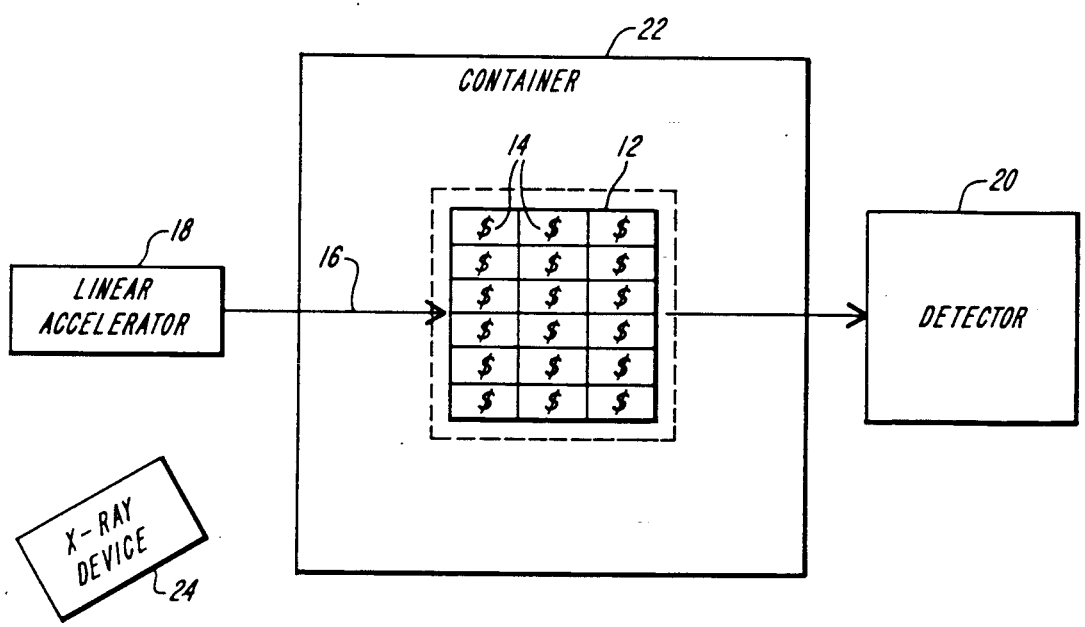
FIG. 1 is a simplified schematic representation in top plan view of an x-ray scanning, neutron detecting system for detecting large concentrations of deuterated paper currency according to the present invention.

With reference to FIG. 1, a mass 12 of paper currency notes 14 is of such a size that when irridatiated by an interrogating beam 16 of a linear accelerator 18 deuterium atoms in the cellulose molecules of the paper notes 14 capture the x-ray photons and undergo a nuclear reaction that emits a high energy neutron, n. A neutron detector 20, preferably a conventional boron triflouride detector, detects and counts the neutrons. The detector is shown arranged in line with the interrogating X-ray beam, but this in line geometry is not required.

A central feature of this invention is that the cellulose comprising each note is deuterated, that is, deuterium atoms are exchanged for or used in place of, hydrogen atoms in the cellulose molecules that form the fibers that in turn make up the currency. In the U.S., paper currency is a combination of 75% cotton and 25% linen, and therefore is primarily cellulose. Cellulose, in turn, is a polymer of $\beta$-D-glucopyranosyl. A typical molecule in the polymer chain contain 31 hydrogen atoms, 18 carbon atoms and 15 oxygen atoms. By weight, the fraction of this molecule which is hydrogen is therefore $31/(31+(18\times12)+(15\times16))=6.4\%$. If the cellulose is fully deuterated, deuterium will constitute 12% of the molecules by weight, $62/(62+(18\times12)+(15\times16))$.

Another central feature of this invention is that the paper currency 14 need not be completely deuterated to be reliably detected, but it must be deuterated at least about 300 times more than taught by Alvarez's U.S. Pat. No. 4,251,726, the disclosure of which is incorporated herein by reference, and preferably at least 1,000 times more. More specifically, Alvarez requires the presence of about $10^{23}$ atoms of deuterium, about 0.3 gram, to produce a reliably detectable signal at a range of a few feet. The present invention, in sharp contrast, requires the presence of at least 100 grams of deuterium, and preferably at least 300 grams.

Because we are interested in detecting only large accumulations of individual units of paper currency, none of which alone, or even in small concentrations we wish to detect, we do not require 100% deuteration of the cellulose forming the paper. For example, if we wish to detect an accumulation 12 of notes 14 having a total value of $1,000,000 with each note valued at $20, the total weight of this mass 12 in U.S. currency is 55 kg. If completely deuterated, it would contain 6.6 kg of deuterium. Since we only need to have, preferably, 300 grams, we can reduce the deuteration from 100% to $300/6600=4.6\%$. As the 300 grams is divided among 50,000 separate notes 14, each note contains $300/50,000=6$ milligrams of deuterium. A deuterated note according to this invention therefore weighs only 0.003 grams more than a conventional, non-deuterated notes.

The cost of deuteration and currency turn over rates are also significant. The typical lifetimes, total number of notes of each denomination typically in circulation, their value and the flux (yearly turnover rate) of each denomination of currency is given below:

| Bill Denomination | Lifetime (Years) | Total $ Value (Billions) | Total No. Of Notes (Billions) | Flux, #/Yr. (Billions) |
|---|---|---|---|---|
| $1 | 1.5 | $4.6 | 4.6 | 3.1 |
| $2 | | $0.76 | | |
| $5 | 2 | $5.8 | 1.2 | 0.58 |
| $10 | 3 | $11.8 | 1.1 | 0.39 |
| $20 | 5 | $63.2 | 3.2 | 0.63 |
| $50 | 9 | $30.1 | 0.6 | 0.067 |
| $100 | 23 | $113 | 1.1 | 0.049 |
| $500 | | $0.15 | | |
| $1000 | | $0.174 | | |
| $5000 | | $0.0018 | | |
| $10000 | | $0.0034 | | |
| Totals | | $230 $\times 10^9$ | 11.8 $\times 10^9$ | 5 $\times 10^9$ |

If the entire U.S. currency is deuterated according value in accordance with this invention (0.3 mg in $1 notes; 6 mg in $20 notes; 30 mg in $100 notes), then the entire $230 billion in circulation would require 70 metric tons of deuterium. The current price of heavy water ($D_2O$) is about $0.10 per gm. Since $D_2$ is 20% deuterium, the deuterium costs about $0.50 per gram. This is less than a penny per $20 note. This is also about $35 million for the material cost of the heavy water to deuterate the entire currency supply, a modest cost compared to the billions of dollar involved in the drug traffic alone, a portion of which could be expected to be intercepted and confiscated using the present invention. Moreover, the U.S. currently has sufficient heavy water in unused inventory to deuterate the entire currency with no new expenditures for the deuterium.

The detection process can use a linear accelerator of the general type described in the Alvarez patent, e.g. a small, commercially available linear accelerator such as the Model 400 Linac sold by Varian with an output of X-rays having an energy of more than 2 MeV. It produces 1 r/min. at 1 meter in a 2 mm spot in 3.9 $\mu$sec pulses. This is eguivalent to a flux of $1.4\times10^9\gamma$/sec.) Of all the known stable (non radioactive) nuclei, only deuterium and beryllium have a small enough threshold to undergo a nuclear reaction when interrogated with such a beam, absorbing the x-ray photon and emitting a neutron. The cross section for this reaction is about $2\times10^{-27}cm^2$.

The detector 20 can be a commercially available boron triflouride neutron detector. The spacing of the detector from the mass 14 of notes is set to be the maximum size of a container 22 surrounding and concealing the mass 12. If the container 22 is a standard commercial cargo container as used in marine shipments, it has an eight foot width. If the mass 12 is located at the center of the container, the detector 20 must reliably detect neutrons produced by the x-ray induced nuclear reaction in the deuterated currency at a range of four feet. (If the mass 12 is near one side, two x-ray units and associated detectors can scan in opposite directions across the container to ensure the desired degree of reliability of detection despite the range.) It should be noted that the interrogation is made and the currency detected, provided the mass 12 is sufficiently large to present at least 100 grams, but preferably at least 300 grams or more of deuterium, without opening the container or injuring any contents of the container. The x-rays involved here will not, for example, expose standard film.

It is important that the deuteration tagging cannot be avoided by shielding o removing the deuterium from the currency. The shielding can be directed against the interrogating x-rays or the emitted neutrons. It is possible to shield current deuterated according to this invention against x-rays by enclosing them in a heavy metal container. For 2 MeV x-rays the absorption length (the intensity being reduced in value to 1/e) is about 33 $gm/cm^3$ in lead. Therefore 3 cm of lead reduces the signal to about 37% of its full value and 6 cm reduces it to about 14% of its full value. Yet the deuterated money of the present invention can be detected even with this 6 cm lead shielding. For large bulks of currency, e.g. 65 kg in $20 notes, the currency can be reduced to a cube about 40 cm on a side. Six cm of lead shielding around from sides would weight over 40 kg, and still be inadequate. Several tons of lead would be required. If this mass of shielding is used and not detected due to its weight, a secondary transmission x-ray device 24 can be employed to find the shielding.

If it is desired to shield the neutrons emitted by the deuterated currency, the high energy (1 MeV and above) neutrons must be thermalized by scattering off hydrogen. But hydrogen rich materials, such as paraffin, have a very low density and therefore require a large volume to achieve the necessary thermalization. Assuming there is sufficient material to thermalize the neutrons, then the neutrons can be absorbed by boron. However, this would place a large amount of boron in the container around the mass 12 of currency, and known methods can .detect the presence of large amounts of boron. In FIG. 1, the device 24 could also serve as a boron detecting apparatus of known construction. In short, shielding of either the x-rays or emitted neutrons is very difficult, and if achieved, would require large and detectable accumulations of the shielding material.

The removal of deuterium through a hydrogen for-deuterium exchange is another possible technigue for avoiding the detection of concentration deuterated money. It is believed that the deuterium carbon bond is sufficiently strong that deuterium will not exchange with hydrogen as a result of a straightforward process of simply soaking the money in water—a true "laundering". If a solvent or other mechanism is found to make such an exchange possible, it can be countered by introducing a dye or the like that will alter the note in the presence of the solvent. Another solution is to place the deuterium in an artificially synthesized cellulose fiber and preferably one with the deuterium buried deeply within the molecule, as compared to the deuterium in naturally occurring cellulose of cotton and linen. A small percentage of such deuterated artificially synthesized fibers can be blended with material fibers, similar to cotton and artificial fiber blends used in textiles for clothing. A blend of 10% to 20% synthetic, deuterated cellulose and 80 to 90% natural cellulose should provide the benefits of the present invention, extra protection against "laundering", and retain much of the "feel" and other characteristics of conventional currency.

The level of deuteration required is related to the background "noise" to the detection process arising from background sources such as the deuterium in normal water, cosmic radiation, and neutrons produced by the decay of uranium in the earth. The main clutter of background deuterium will come from materials with high water content. A mass of a million dollars in notes contains, according to this invention, preferably at least 300 grams of deuterium. This is the same amount of deuterium as found in one ton of water (a container of water about 1 meter on a side, or about five 55 gallon drums). This level of background clutter is not a problem for a $1,000,000 mass, but it may become significant for the reliable detection of masses totally in value $100,000 or less. If it is desired to detect concentrations of such smaller total dollar amounts, then it is necessary to increase the level of deuteration above a minimum 0.1 mg per $1.00 value per note, and perhaps even above the preferred value of 0.3 mg per $1.00 value per note.

The safety of a currency deuterated to a level according to the present invention is also a significant consideration. Deuterium is itself not radioactive. Ordinary water contains deuterium as $D_2O$, with deuterium comprising 300 ppm by weight. The water in a 170 pound man contains 2.4 grams of deuterium. One note deuterated according to this invention contains 0.006 gram. This is less deuterium than is found in a cup of water. Deuterated money is thus no more toxic than drinking water. If a child eats a note of currency deuterated in accordance with this invention, there will be no risk to the child; the only concerns will be the loss of the money and the eating habits of the child.

The x-ray process, of course, presents risks to those in the vicinity of the x-ray beam. The x-ray emitter described above, however, is similar to a device presently in use for verification of the recent arms control treaty between the U.S. and the U.S.S.R. Safety procedures acceptable for the x-ray verification can suffice for bulk money detection. And it should be noted that the x-rays interrogation of containers does not render the containers or their contents radioactive. In short, the currency and detection process of the present invention are safe; they do not present a nuclear radiation hazard, a toxicity hazard if the currency is ingested, or an x-ray irradiation hazard provided normal precautions are used in operating the x-ray equipment.

It should be noted that in addition to posing no public health problem, currency deuterated according to the present invention cannot invade the privacy of individuals. A person carrying or transporting eve relatively large amounts of cash, e.g. $10,000 would not have a sufficient concentration of cash to be detectable. Moreover, cash in any amount must pass under an x-ray beam. Clearly this is not the sort of arrangement that would be employed in any broad scale way to inspect for cash carried on persons. As to the inspection of articles, e.g. luggage carried on airplanes, there can be a safe inspection, but the concentration of deuterium will not be sufficient to rise above the threshold for reliable detection.

A paper currency and a method for detecting large concentrations of such currency has been disclosed which is non destructive, safe, reliable, operable at ranges sufficient to inspect even large cargo containers currently in use, while not invading the privacy of citizens engaged in lawful activities or posing an extreme cost. The detection system of this invention is also highly resistant to avoidance by shielding. Even large amounts of metal shielding such as would normally block interrogating beam or the emission of tell tale gases are not sufficient to interfere with the operation of this invention.

While the invention has been described with respect to its preferred embodiments, it will be understood that various modifications and variations will occur to those skilled in the art. For example, while the invention has been described with respect to the detection of large quantities of U.S. currency, it can readily be modified to detect large concentrations of other currencies, negotiable paper or the like with the proper adjustment in the ratio of deuterium per value of the associated note. Also, while the invention has been expressed in deuteration levels for U.S. currency, the values stated assume the current 1990 value of U.S. currency. If, for example, there was strong inflation, then deuteration levels would be adjusted to keep pace with significant cumulative changes in value of the currency. The invention can also be extended beyond paper currency and other paper products, provided that the product integral or some component of the product contains hydrogen which can be substituted by deuterium and the level of deuteration is selected so that the item or collection of items to be detected contains sufficient deuterium to be detected at the appropriate range. Deuterating the materials forming the housing of controlled electronic equipment is one such application. These and other modifications and variations are intended to fall within the scope of the following claims.

What is claimed is:

1. A note of monetary currency comprising a sheet formed principally of cellulose that is deuterated to a level that results in at least 0.1 mg of deuterium for each one dollar (U.S.) in value of the note.

2. A currency note according to claim 1 wherein said cellulose material comprises a portion of natural, undeuterated fibers and a portion of synthetic, deuterated fiber.

3. A currency note according to claims 1 or 2 further comprising a dye incorporated in said material which is activated by any solvent that would exchange deuterons for hydrogen atoms in said cellulose fibers.

4. A currency note according to claim 2 wherein said synthetic portion constitutes between 10 and 20% by weight of the note.

5. A currency note according to claim 1 wherein said level of deuteration is at least 0.3 mg of deuterium for each one dollar (U.S.) in value of the note.

6. A method for detecting large concentrations of monetary currency in the form of sheets of principally a cellulose material comprising, deuterating each sheet so that it contains at least 0.1 mg of deuterium for each $1.00 (U.S.) in value of the note, interrogating the concentration of deuterated notes with a photon beam in the x-ray spectrum having an energy of at least 2 MeV, and detecting the neutrons produced by the interrogation.

7. The method of claim 6 further comprising the step of altering the currency note so that the use of a solvent to promote an exchange of hydrogen for deuterons will be detectable.

8. The method of claim 7 wherein said altering comprises adding a dye to said currency notes.

9. The method of claim 6 further comprising means for detecting shielding capable of screening said interrogating beams from said currency concentration.

10. The method of claim 6 further comprising means for detecting boron concentrations that can capture neutrons produced by said interrogating.

* * * * *